United States Patent [19]

Epstein

[11] Patent Number: 5,885,593
[45] Date of Patent: *Mar. 23, 1999

[54] SKIN CARE COMPOSITION INCLUDING CYCLODEXTRIN MATERIALS AND METHOD FOR TREATING SKIN THEREWITH

[75] Inventor: Howard Epstein, Rochester, N.Y.

[73] Assignee: The Andrew Jergens Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 682,333

[22] Filed: Jul. 17, 1996

Related U.S. Application Data

[60] Provisional application No. 60/005,692, Sep. 28, 1995.

[51] Int. Cl.$^6$ ....................................... A61K 7/48
[52] U.S. Cl. ..................... 424/401; 514/557; 514/844; 514/847; 514/873
[58] Field of Search ............................ 424/401; 514/557, 514/844, 847, 873

[56] References Cited

U.S. PATENT DOCUMENTS

| | | | |
|---|---|---|---|
| 3,879,537 | 4/1975 | Van Scott | 424/311 |
| 3,920,835 | 11/1975 | Van Scott | 424/311 |
| 3,984,566 | 10/1976 | Van Scott | 424/283 |
| 4,105,783 | 8/1978 | Yu | 424/283 |
| 4,197,316 | 4/1980 | Yu | 424/317 |
| 4,234,599 | 11/1980 | Van Scott | 424/279 |
| 4,380,549 | 4/1983 | Van Scott | 424/317 |
| 4,389,418 | 6/1983 | Burton | 424/365 |
| 5,091,171 | 2/1992 | Yu | 424/642 |
| 5,476,852 | 12/1995 | Cauwenbergh | 514/252 |
| 5,648,380 | 7/1997 | Martin | 514/461 |
| 5,674,912 | 10/1997 | Martin | 514/724 |

FOREIGN PATENT DOCUMENTS 4-74107  3/1992  Japan .

OTHER PUBLICATIONS

"Hydroxy Acids and Skin Aging," *Cosmetics & Toiletries Magazine*, vol. 109, Sep. 1994, pp. 41–48.
Brochure: "β Cyclodextrin Kleptose®, The New Approach to Molecular Encapsulation" by Roquette Fréres, 1992.
Brochure: "Cavitron Cyclo–Dextrins, A Breakthrough for Molecular Encapsulation," by Amaizo, 1991.
"Solving Problems with Cyclodextrins in Cosmetics," *Cosmetics & Toiletries Magazine*, vol. 108, Nov. 1994, pp. 90–95.

*Primary Examiner*—José G. Dees
*Assistant Examiner*—Michael A. Williamson
*Attorney, Agent, or Firm*—Oblon, Spivak, McClelland, Maier & Neustadt, P.C.

[57] ABSTRACT

There is disclosed a method for treating skin along with a novel skin care composition comprising the following components in a suitable carrier:

(a) from about 1 to about 10 weight percent of a cyclodextrin material; and (b) from about 1 to about 15 weight percent of an acid material selected from:
alpha hydroxy acids, beta hydroxy acids, alpha keto acids, beta keto acids, and combinations thereof.

The skin care composition includes a cyclodextrin material to reduce the irritation and stinging caused by the presence of the aforementioned acid materials.

18 Claims, No Drawings

SKIN CARE COMPOSITION INCLUDING CYCLODEXTRIN MATERIALS AND METHOD FOR TREATING SKIN THEREWITH

This application claims the benefit of U.S. Provisional Application No(s).: 60/005,692, filed Sep. 28, 1995.

FIELD OF THE INVENTION

The present invention generally relates to the use of cyclodextrin materials to reduce the irritation and stinging caused by acid materials, e.g. alpha hydroxy acids, used within skin care compositions.

BACKGROUND OF THE INVENTION

Alpha and beta hydroxy (and keto) acids have been used in a wide variety of skin care compositions to remove dead cells from the surface of the skin and to assist in skin moisturization. See U.S. Pat. Nos. 3,879,537, 3,920,835, 3,984,566, 4,105,783, 4,197,316, 4,234,599, 4,380,549, and 5,091,171. Also see Smith, W. P., "Hydroxy Acids and Skin Aging," Cosmetics & Toiletries, Vol. 109, pp. 41–48 (September, 1994). Such acids are of interest in skin care compositions because of the demand for products that diminish the appearance of fine lines on the face and improve the appearance of flaking or dry skin. Although such acid materials offer a number of advantages, they also commonly cause skin irritation and stinging, particularly when used in effective concentrations, i.e. greater than about 1 weight percent, and more commonly around 3 to about 15 weight percent. The irritation caused by such acid materials is most noticeable in applications of skin care compositions to sensitive skin areas, e.g facial application. As such, the application such skin care compositions are often limited.

SUMMARY OF THE INVENTION

The present invention is directed toward reducing the irritation and stinging associated with skin care composition including alpha and beta hydroxy and/or alpha and beta keto acids in amounts greater than about 1 weight percent and typically between about 3 to about 15 weight percent. The present invention includes the use of cyclodextrin materials which significantly reduces the aforementioned irritation. More specifically, the present invention includes a method for treating skin along with a skin care composition comprising the following components in a suitable carrier:

(a) from about 1 to about 10 weight percent of a cyclodextrin material;

(b) from about 1 to about 15 weight percent of an acid material selected from:
  alpha hydroxy acids, beta hydroxy acids, alpha keto acids, beta keto acids, and combinations thereof.

DETAILED DESCRIPTION OF THE INVENTION

The present invention includes a method for treating skin along with a skin care composition used therein. The present method comprises the step of applying the subject skin care composition to the skin, wherein the subject skin care composition comprises the following components in a suitable carrier:

(a) from about I to about 10 weight percent of a cyclodextrin material;

(b) from about 1 to about 15 weight percent of an acid material selected from:
  alpha hydroxy acids, beta hydroxy acids, alpha keto acids, beta keto acids, and combinations thereof.

The skin care composition of the present invention may comprise both oil-in-water (water-out) emulsions and water-in-oil (oil-out) emulsions. Such emulsions and their formulation are well known in the art. Emulsifiers employed such formulations have traditionally included anionic (e.g. sodium lauryl sulfates, ammonium stearate, sulfated castor oil, dioctyl sodium sulfosuccinate), nonionic (e.g. PEG gylceryl), amphoteric, cationic, and mixtures thereof. By way of example, U.S. Pat. No. 4,389,418 to Burton discloses a skin care compositions including a cationic emulsifier, i.e. a quaternary ammonium compound. Another example of a nonionic formulation is provided in the example section below.

The cyclodextrins used in the present invention are cyclicoligosaccarides produced by the enzymatic degradation of starch and have multiple glucose or glucopyranose units, usually 6 to 8 units. Depending on the particular preparation reaction conditions employed, cyclodextrins generally contain six, seven or eight of such units, connected by alpha-(1,4) bonds. The six, seven or eight unit cyclodextrins are commonly known as alpha-, beta-, and gamma-cyclodextrins, respectively. A particularly preferred beta-cyclodextrin material is available from Amaizo American Maize-Products Co. under the trade no. 410-105.

Cyclodextrins are well known and are commercially produced by the enzymatic degradation of starch. For example, beta-cyclodextrin is the major product of the reaction between the enzyme cyclodextrin transglycosylase and a starch solution pretreated with gamma-amylase.

Cyclodextrins have the shape of truncated cones with primary and secondary hydroxyl groups located at opposite ends of the torus. The glucosyl-o-bridges point into the center of the molecule and the primary hydrogel groups project from one outer edge while the secondary hydroxyl groups project from the other edge. The result is a molecule with a relatively hydrophobic center and a hydrophilic outer surface. These shapes and hydrophilic/hydrophobic domains provide for inclusion or incorporation of guest molecules into the center of the molecule.

As used herein, the term "cyclodextrins" includes cyclodextrin derivatives, such as cyclodextrin carbonates, ethers, esters, and polyethers; polymers or copolymers of polymerized cyclodextrins, such as polymerized beta-cyclodextrins; and substituted cyclodextrins such as those with functional groups bonded to one or more of the hydroxyl groups. Suitable function groups include, but are not limited to, methyl, ethyl, hydroxyethyl, and hydroxypropyl and acetyl groups. Cyclodextrins of particular applicability to the present invention include hydroxyalkyl beta cyclodextrins, e.g. hydroxy propyl and hydroxy ethyl beta cyclodextrin, beta cyclodextrin crosslinked with epichlorohydrin, and other modified cyclodextrins such as those commercially available from the Amaizo, American Maize-Products Company under the Cavitron Cyclo-dextrins™ mark.

Acid materials applicable to the present invention include alpha and beta hydroxy acids and alpha and beta keto acids. Such acid materials are well known for use in skin care compositions and are described in U.S. Pat. Nos. 3,879,537, 3,920,835, 3,984,566, 4,105,783, 4,197,316, 4,234,599, 4,380,549, and 5,091,171. Such materials should be pharmaceutically acceptable and have an acidic disassociation constant ($pK_a$) within the range of about 1 to about 6, preferably about 2.5 to about 5.0 (measured at 25° C.), and more preferably about 3 to about 4.

Hydroxy polycarboxylic acids may be provided as the alpha or beta analogs and may be present as free acids, peroxides, lactones, amides, esters, or salts. Illustrative of the variety of acids included are saccharic acid, 2-hydroxyglutaric acid, 3,4-dihydroxyglutamic acid, 2,5-dihydroxy-6-aminohexanoic acid, acetopyruvic acid, acetyl pyruvic acid, beta-fluoropyruvic acid, tartaric acid, citric acid, 2-hydroxybenzoic acid (salicylic acid), 2-hydroxy-2-methylbutyric acid, 2-hydroxy isobutyric acid, mandelic acid, and 2-hydroxy caproic acid.

One class of applicable acids are hydroxy, dihydroxy, and keto analogs of amino acids. Examples include glycolic acid, lactic acid, pyruvic acid, glyceric acid, malic acid, beta phenyl lactic acid, beta phenyl pyruvic acid, alpha hydroxy isovaleric acid, alpha hydroxy isocaproic acid, 2,3-dihydroxybutanoic acid, and 2,6-dihydroxyhexanoic acid. Other acids include those selected from the group consisting of citric acid, glycolic acid, glucuronic acid, galacturonic acid, alpha hydroxybutyric acid, alpha hydroxyisobutyric acid, lactic acid, malic acid, mandelic acid, mucic acid, pyruvic acid, alpha phenylactic acid, alpha phenylpyruvic acid, saccharic acid, tartaric acid, tartronic acid, and mixtures thereof.

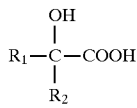

wherein $R_1$ and $R_2$ are hydrogen or an aliphatic hydrocarbon having 1 to 10 carbon atoms which may include substituent hydroxy, carboxyl, and/or ester groups. Preferably, $R_1$ is hydrogen and $R_2$ is hydrogen or an alkyl group having from 1 to 4 carbon atoms. Particularly preferred materials within this class are acids selected from the group consisting of glycolic acid, lactic acid, tartaric acid, malic acid, and mixtures thereof. Still more preferred materials within this class are selected from the group consisting of glycolic acid, lactic acid, and mixtures thereof.

The amount of acid material added to the formulation should be sufficient to adjust the pH of the finished emulsion to a value in the range of about 2.5 to about 4.5, preferably 3.0 to 4.0, measured at 25° C. In particularly preferred embodiments, the amount of acid material in the composition is within the range from about 1 to about 15 weight percent, more preferably about 3 to about 15 weight percent, and still more preferably from about 5 to about 7 weight percent.

The subject skin care composition includes a suitable carrier which acts as a solubilzing agent to help the various components of the composition remain dispersed. The selection of the carrier will depend of course on the specific components utilized in the composition. Examples of applicable carriers include various humectants, fatty alcohols, fatty ester emollients. Specific examples include benzoate esters, myristyl, and myristate.

Humectants act as hygroscopic agents, increasing the amount of water held in the stratum corneum and contributing to the softening of the skin surface. The humectants employed in the formulations of this invention are water-soluble and are substantially nonionizable. By "substantially non-ionizable" is meant no significant or detectable disassociation in water. Suitable humectants for the formulations of this invention include glycerin, propylene glycol, sorbitol polyethylene glycol 1,2,6-hexanetriol hydrogenated starch hydrolysate, inositol, mannitol PEG-5 pentaerythritol ether, polyglyceryl sorbitol xylitol sucrose, and the like. Glycerin is a particularly preferred humectant.

The humectant is preferably present in the composition of this invention at concentrations of about 1 to about 40 weight percent, more preferably about 1 to about 20 weight percent, and still more preferably about 5 to about 15 weight percent.

The subject skin care composition may include additional components such as (a) petrolatum or mineral oil, (b) fatty alcohols, (c) fatty ester emollients, (d) silicone oils or fluids, and (e) preservatives. These components must in general be safe for application to the human skin and must be compatible with the other components of the formulation. Selection of these components is generally within the skill of the art. The following discussion refers to components in the singular although it will be understood that combinations or mixtures are intended to be included as well.

The petrolatum or mineral oil component selected will generally be USP or NF grade. The petrolatum may be white or yellow. The viscosity or consistency grade of petrolatum is not narrowly critical. Petrolatum can be partially replaced with mixtures of hydrocarbon materials which can be formulated to resemble petrolatum in appearance and consistency. For example, mixtures of petrolatum with microcrystalline wax, paraffin wax, and the like may be melted together. Preferred mineral oils are white mineral oils having a viscosity of 6.7 to 69 centistokes at 40° C., a specific gravity (SG 15.6° C./15.6° C.) of 0.828 to 0.890, and a maximum pour point of −18° to −7° C. Still more preferred mineral oils have a viscosity of 6.7 to 17.0 centistokes at 40° C., a specific gravity of 0.828 to 0.860, and a maximum pour point of about −7° to −10° C.

When used the petrolatum or mineral oil component is included in the formulations at a concentration of about 1 to about 10 weight percent, more preferably about 2 to about 6 weight percent. Higher concentrations sometimes lead to an undesirable texture.

Fatty alcohols (typically monohydric alcohols) used in the formulations of this invention stabilize the emulsion and provide a cosmetically acceptable viscosity. Selection of the fatty alcohol is not narrowly critical although $C_{12}$ to $C_{32}$, preferably $C_{14}$ to $C_{22}$, substantially saturated alkanols will generally be employed. Examples include stearyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols.

When used the fatty alcohol is preferably included in the formulations of this invention at a concentration within the range from about 1 to about 8 weight percent, more preferably about 2 to about 4 weight percent. Higher concentrations sometimes lead to an undesirable texture.

Fatty ester emollients enhance the tactile properties of the composition. Examples of suitable fatty esters for use in the formulation of this invention include isopropyl myristate, isopropyl palmitate, isopropyl isostearate, isostearyl isostearate, diisopropyl sebacate, propylene glycol dipelargonate, 2-ethylhexyl isononoate, 2-ethylhexyl stearate, $C_{12}$–$C_{16}$ fatty alcohol lactate, isopropyl lanolate, 2-ethyl-hexyl salicylate, and mixtures thereof. The presently preferred fatty ester is isopropyl palmitate.

When used the fatty ester emollient is preferably included in the formulations of this invention at a concentration of about 1 to about 8 weight percent, more preferably about 2 to about 5 weight percent.

Silicone oils or fluids are used to improve the lubricity of the composition during application to the skin. Preferably the viscosity of the silicone component at a temperature of 25° C. is from about 5 to about 12,500 centistokes. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone—a dimethylpolysiloxane endblocked with trimethyl units—is presently preferred. Dimethicone having a viscosity between 10 and 1000 centistokes is particularly preferred.

When used the silicone oils are preferably included in the formulations of this invention at a concentration of about 0.1 to about 10 weight percent, more preferably about 1 to about 2 weight percent. Due to expense, higher concentrations of silicone oils are typically avoided.

The formulation may also contain other conventional additives employed in cosmetic emulsions. Such additives include aesthetic enhancers, fragrance oils, dyes, preservatives, sun screen additives, and medicaments such as menthol and the like. Preferred aesthetic enhancers are polyquaternium 31 and aluminum starch octenylsuccinate.

As an illustration of the present invention, several examples are provided below. These examples serve only to further illustrate aspects of the invention and should not be construed as limiting the invention.

EXAMPLES

Two substantially similar nonionic emulsion skin care compositions were prepared and tested according to the procedures provided below. The first composition included 3.50 weight percent cyclodextrin material, whereas the second composition included no cyclodextrin. The individual constituents and their relative amounts for each composition are provided in Table I below.

The example skin care compositions were prepared by first making four individual phases, as identified in Table I. These individual phases were prepared by mixing the identified constituents in the relative amounts as provided in Table I. Following their preparation, the individual phases were heated to the following temperatures; first phase—approximately 75° C., second phase—approximately 82° C., third phase—approximately 39° C., fourth phase—approximately 35° C. Subsequently, the second phase was added to the first, with continuous mixing, followed by cooling to about 39° C. The third phase was pH adjusted to approximately 3.30 and added to the previously combined first and second phases, followed by mixing and cooling to approximately 35° C. Subsequently, the forth phase was added with continuos mixing, followed by cooling of the composition to room temperature.

| Constituent | Skin Care Composition with Cyclodextrin | Skin Care Composition without Cyclodextrin |
|---|---|---|
| | Percent by Weight | |
| First Phase (water) | | |
| water | 39.90 | 43.40 |
| β-cyclodextrin (from Amaizo American Maize Products Co.) | 3.50 | |
| Cellulose Gum (from TIC Gums, Inc., Belcamp, MD as "TIC-X-200") | 0.20 | 0.20 |
| Glycerin (from Procter & Gamble) | 6.00 | 6.00 |
| Methyl paraben (preservative, from Inolex Chemicals as "TEG.M") | 0.30 | 0.30 |
| Second Phase (oil) | | |
| Polyol prepolymer-2 (from Penederm Inc.) | 3.00 | 3.00 |
| Lipid Soya sterol (from Henkel Co., as "Generol 122-E-10") | 1.00 | 1.00 |
| Triglycerides Mixture (from Huls America as "Miglyol 812") | 5.00 | 5.00 |
| Stearic Acid (from Witco Chemical) | 2.50 | 2.50 |
| Cetyl Ester (from Rhone-Poulenc as "Dermalcare SPS") | 2.00 | 2.00 |
| Silcone Fluid (D.C. 345 from Dow Corning) | 4.00 | 4.00 |
| Silicone Fluid (D.C. 200 from Dow Corning) | 2.00 | 2.00 |
| Emulsifier (from Lipo Chemicals as "Lipowax NI") | 2.00 | 2.00 |
| Emulsifier (from Lipo Chemicals as "Lipowax 165") | 1.50 | 1.50 |
| Emulsifier (from Lipo Chemicals as "Lipocol S-2") | 0.50 | 0.50 |
| Isoproyl propyl palmitate (from Amerchol Co.) | 2.00 | 2.00 |
| Third Phase (water) | | |
| water | 15.00 | 15.00 |
| 70% glycolic acid (from Dupont Corp.) | 5.00 | 5.00 |
| lactic acid (from Barnet Products as "Biolac") | 2.00 | 2.00 |
| Ammonium Hydoxride (from Spectmm Chemical Co.) | 1.00 | 1.00 |
| Fourth Phase (water) | | |
| water | 1.00 | 1.00 |
| Preservative (from ISP Co. as "Germall II") | 0.25 | 0.25 |

-continued

| Constituent | Skin Care Composition with Cyclodextrin | Skin Care Composition without Cyclodextrin |
|---|---|---|
| | Percent by Weight | |
| Fragrance (from Hogan Fregrances as "Hogan K92-10820") | 0.35 | 0.35 |
| pH of Composition | 3.30 | 3.30 |

The two skin care compositions were tested as follows. A panel of healthy, adult females between the ages of 18 and 60 years were selected on the basis of a prescreening test described below.

The inclusion criteria were:
(1) Women between the ages of 18 and 60 years in good general health who are not currently under a doctor's care for any medical condition.
(2) Women with no history of hypertension, cardiovascular disease, diabetes, ocular disease or chronic skin diseases.
(3) Women with Fitzpatrick skin types I, II or III.
(4) Healthy, adult, white female volunteers who have been selected from a prescreening stinging test by obtaining a cumulative stinging score of 3.0 (sum of 2.5 and 5.0 minute reports) or greater with 10% lactic acid on a four-point ordinal scale. In order to minimize confounding treatment responses due to intense stinging on one side of the face, no more than two subjects who report severe stinging were included per 12 patient panel. Panelists were selected such that their combined cumulative stinging score will be approximately 45.
(5) Women who wear waterproof facial makeup must be willing to refrain from using it on the day of the study.
(6) Women who wear facial makeup must be willing to remove it at least 1 hour before study initiation.
(7) Women willing to refrain from using commercial sunscreen products on the day of the study.
(8) Women willing to refrain from using facial moisturizers or lotions on the day of the study.

The exclusion criteria were:
(1) Women who exhibit photosensitivity or other dermatoses or recent sunburn on the face.
(2) Women who have used systemic or topical treatments with steroids, anti-inflammatory agents or antihistamines in the 7 days prior to study initiation.
(3) Women who present themselves on the study day with obvious facial irritation as determined by the investigator.
(4) Women who are pregnant or lactating.
(5) Women having a history of hypersensitivity to topical cosmetics, sunscreens, moisturizers or other toiletries.
(6) Women having sunburn or prolonged sun exposure to the face.

The method for this test was based on the procedure described by Grove, et al.: "Guidelines for Performing Facial Stinging Tests", proceedings of the 12th International Congress of the I.F.S.C.C., Paris, France, 1982, and is based on selecting individuals who are likely to experience stinging on the face following the application of topical products.

Pre-screening:
The pre-screening test was conducted at room temperature (22° C.) with non-perspiring subjects. A liberal amount of an aqueous 10% solution of lactic acid was thoroughly rubbed over the nasolabial fold and cheek with a cotton-tipped applicator. Stinging was evaluated at 2.5 and 5.0 minutes after application by asking the subject to grade the intensity of stinging by using a four-point ordinal scale:
0=no stinging
1=slight
2=moderate
3=severe stinging The cumulative stinging score for an individual is the sum of these grades. Those candidates who cumulative stinging score is 0 are considered non-stingers. Candidates with a cumulative score greater than 0 but less than 3 are considered slight stingers. Candidates with a cumulative score greater than 3 but less than 6 are considered moderate stingers. Candidates with a cumulative score equal to or greater than 6 are considered severe stingers. During this pre-screening procedure, water was applied concurrently to the opposite side of the face to ensure that the individual could reliably distinguish a sting response. The 10% aqueous lactic acid probe and water control were prepared by the investigator and placed in identical containers labeled as "Test solution D" for 10% lactic acid and "Test solution C" for the water control. Applications of test solutions D and C to the left and right sides of the face were balanced by a randomization schedule prepared by the investigator.

A group of 12 Caucasian females were selected on the basis of the inclusion criteria as listed in the protocol and on their ability to develop a stinging response to lactic acid. Their ages ranged from 18 to 56 years.

The pre-screening total stinging scores for this group of women with test solution D (lactic acid) are shown in the enclosed Table 2. There was no stinging experienced with solution C (water) while the total cumulative stinging score with solution D was 43.0. This group of women was therefore judged to be prone to develop facial stinging and hence suitable for subjectively assessing the stinging potential of topically applied products.

TABLE II

| Subject Number | Total Stinging Score |
|---|---|
| 1 | 4 |
| 2 | 3 |
| 3 | 3 |
| 4 | 3 |
| 5 | 3 |
| 6 | 5 |
| 7 | 4 |
| 8 | 5 |
| 9 | 3 |
| 10 | 3 |
| 11 | 4 |
| 12 | 3 |
| Stinging Capacity Scores: | 43.0 |

Test Procedure:
Immediately prior to the actual test, the subjects were instructed to wash the whole face with non-scented Neutrogena Facial Bar (Neutrogena Original Formula, lot #6110-G1) which was supplied by the investigator. After lathering the soap and applying to their faces with their hands, the subjects rinsed with water and then blotted their faces dry with fresh hand towels. All makeup, if present, was removed by the subject one hour prior to initiating the study.

The actual test was conducted in an environmental chamber set at 120° F. and 40% relative humidity, where the subject were brought to a state of profuse sweating. A liberal amount of the skin care composition including cyclodextrin was then thoroughly rubbed over the nasolabial fold and cheek area of each subject to one side of the face with a cotton-tipped applicator, while the opposite side received the skin care composition including no cyclodextrin. Applications to each side were randomized. Stinging was evaluated at 2.5 and 5.0 minutes after product application by asking each subject to grade the intensity of stinging using the aforementioned four-point scale. The cumulative stinging score for an individual was the sum of these two grades.

One week later, the subjects were recalled and tested again exactly as described above. The second test product was applied to one side of the face while the same control was applied to the opposite side. Again product applications were randomized. The stinging capacity of each test material was evaluated by using the following scale which is based on the combined cumulative stinging scores:

<10 Little or no potential for stinging during normal intended use.

11–24 Slight potential for stinging which could pose a problem for certain individuals with very sensitive skin.

>25 Strong potential for stinging; will be very likely to cause problems especially in sensitive individuals and perhaps other consumers as well.

The results of the stinging test with the example skin care compositions are shown in Table III. The total stinging score for the skin composition with cyclodextrin was 3.0 compared to a total score of 11.0 for the skin care composition with no cyclodextrin.

TABLE III

| Subject No. | Composition with Cyclodextrin | | | Composition without Cyclodextrin | | |
|---|---|---|---|---|---|---|
| | 2.5 Minutes | 5.0 Minutes | Cumulative | 2.5 Minutes | 5.0 Minutes | Cumulative |
| 1 | 2 | 1 | 3 | 2 | 2 | 4 |
| 2 | 0 | 0 | 0 | 0 | 1 | 1 |
| 3 | 0 | 0 | 0 | 0 | 1 | 1 |
| 4 | 0 | 0 | 0 | 0 | 0 | 0 |
| 5 | 0 | 0 | 0 | 0 | 0 | 0 |
| 6 | 0 | 0 | 0 | 2 | 3 | 5 |
| 7 | 0 | 0 | 0 | 0 | 0 | 0 |
| 8 | 0 | 0 | 0 | 0 | 0 | 0 |
| 9 | 0 | 0 | 0 | 0 | 0 | 0 |
| 10 | 0 | 0 | 0 | 0 | 0 | 0 |
| 11 | 0 | 0 | 0 | 0 | 0 | 0 |
| 12 | 0 | 0 | 0 | 0 | 0 | 0 |
| Stinging Capacity Scores: | | | 3 | | | 11 |

Many other modifications and variations of the present invention are possible to the skill pactitioner in the field in light of the teachings herein. It is therefore understood that, within the scope of the claims, the present invention can be practiced other than as herein specifically described.

I claim:

1. A skin care composition comprising at least one or more agents which irritate human skin upon application thereto, wherein all of which said agents which irritate human skin upon application thereto are selected from the group consisting of alpha-hydroxy acid, beta hydroxy acid, alpha keto acid, beta keto acid, and combinations thereof, and wherein said skin composition further comprises an amount of a cyclodextrin material sufficient to reduce irritation caused by application of said agents, in an amount of 1 to about 10 weight percent.

2. The composition of claim 1 wherein the pH of said composition is within the range from about 3.0 to about 4.0.

3. The composition of claim 1 comprising from about 5 to about 7 weight percent acid material.

4. The composition of claim 1 wherein said composition includes an alpha hydroxy acid represented by the formula:

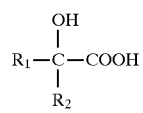

wherein $R_1$ and $R_2$ are independently selected from: hydrogen, and alkyl groups having from 1 to 10 carbon atoms wherein said alkyl groups may be substituted with hydroxy and/or carboxyl groups.

5. The composition of claim 4 wherein $R_1$ is hydrogen, and $R_2$ is an alkyl group having from 1 to 4 carbon atoms wherein said alkyl group may be substituted with hydroxy and/or carboxyl groups.

6. The composition of claim 5 wherein said alpha hydroxy acid is selected from the group consisting of glycolic acid, lactic acid, and mixtures thereof.

7. The composition of claim 1 wherein said cyclodextrin material is beta-cyclodextrin.

8. The composition of claim 1 wherein said carrier includes at least one of: humectant, emollient, and a fatty alcohol.

9. The composition of claim 1 wherein said composition includes a humectant.

10. The composition of claim 9 wherein said humectant is water-soluble and substantially non-ionizable.

11. The composition of claim 9 wherein said humectant is selected from the group consisting of: propylene glycol, polyethylene glycol, sorbitol, glycerin and combinations thereof.

12. The composition of claim 9 including from about 1 to about 20 weight percent glycerin.

13. The composition of claim 1 further including: petrolatum, mineral oil or combinations thereof.

14. The composition of claim 1 further including at least one of: a fatty alcohol, a fatty ester emollient, and a silicone fluid.

15. A method for treating skin, comprising the step of applying a skin composition of claim 1 to said skin.

16. The method of claim 15 wherein the pH of said composition is within the range from about 3.0 to about 4.0 and the composition includes an alpha hydroxy acid represented by the formula:

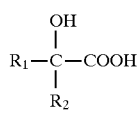

wherein $R_1$ and $R_2$ are independently selected from: hydrogen, and alkyl groups having from 1 to 10 carbon atoms wherein said alkyl groups may be substituted with hydroxy and/or carboxyl groups.

17. The method of claim 16 wherein the alpha hydroxy acid is selected from the group consisting of: glycolic acid, lactic acid, and mixtures thereof.

18. The method of claim 15 wherein the composition includes at least one of: humectant, emollient, fatty alcohol, and silicone fluid.

* * * * *